(12) United States Patent
Carminati et al.

(10) Patent No.: US 7,799,921 B2
(45) Date of Patent: Sep. 21, 2010

(54) STEREOSELECTIVE PROCESS AND CRYSTALLINE FORMS OF A CAMPTOTHECIN

(75) Inventors: Paolo Carminati, Rome (IT); Maria Ornella Tinti, Rome (IT); Mauro Marzi, Rome (IT); Fabrizio Giorgi, Rome (IT); Walter Cabri, Rodano (IT); Marco Alpegiani, Rodano (IT); Domenico Vergani, Rodano (IT); Paolo Ghetti, Rodano (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 642 days.

(21) Appl. No.: 11/721,282

(22) PCT Filed: Dec. 16, 2005

(86) PCT No.: PCT/EP2005/056849

§ 371 (c)(1),
(2), (4) Date: Jun. 8, 2007

(87) PCT Pub. No.: WO2006/067092

PCT Pub. Date: Jun. 29, 2006

(65) Prior Publication Data

US 2009/0239893 A1   Sep. 24, 2009

(30) Foreign Application Priority Data

Dec. 21, 2004 (EP) ................... 04030246

(51) Int. Cl.
C07D 471/00 (2006.01)
A01N 43/42 (2006.01)
(52) U.S. Cl. .......................................... 546/48; 514/283
(58) Field of Classification Search ................. 514/283; 546/48
See application file for complete search history.

(56) References Cited

FOREIGN PATENT DOCUMENTS

EP        1 044 977 A1    3/1999
WO     WO 03/074527      9/2003

OTHER PUBLICATIONS

Dallavalle et al. Journal of Medicinal Chemistry, 2001, 44, 3264-3274.*
Dallavalle, Journal of Medicinal Chemistry, 2001, 44, 3264-3274.*
Sabrina Dallavalle, et al., Novel 7-Oxyiminomethyl Derivatives of Camptothecin . . . , J. Med. Chem. vol. 44, pp. 3264-3274, 2001, XP-002307863.
Mino R. Caira, Crystalline Polymorphism of Organic . . . , Topics Current Chemistry, vol. 198, pp. 163-208, XP001156954.
Rossi, et al., Structural Studies on ST1481 . . . , Acta Ceryst., vol. a61, pp. C275, 2005, XP002388924.

* cited by examiner

*Primary Examiner*—D. Margaret Seaman
*Assistant Examiner*—Nizal S Chandrakumar
(74) *Attorney, Agent, or Firm*—Lucas & Mercanti, LLP

(57) ABSTRACT

A stereoselective process for preparing 7-[(E)-t-butyloxyiminomethyl]-camptothecin (also known as gimatecan) is herein disclosed. With the addition of further dissolution and precipitation steps carried out in appropriate different solvent mixtures, four new crystalline forms of gimatecan are also obtainable by using the same stereoselective process.

22 Claims, 4 Drawing Sheets

Form I

Form II

Form III

STEREOSELECTIVE PROCESS AND CRYSTALLINE FORMS OF A CAMPTOTHECIN

FIELD OF THE INVENTION

This invention relates to a stereoselective process for preparing 7-[(E)-t-butyloxyiminomethyl]-camptothecin (also known as gimatecan). With the addition of further dissolution and precipitation steps carried out in appropriate different solvent mixtures, three new crystalline forms of gimatecan are obtainable by using the same stereoselective process

BACKGROUND OF THE INVENTION

Camptothecin is an alkaloid, which was isolated by Wall et al (*J. Am. Chem. Soc.* 88, 3888-3890 (1966)) for the first time from the tree *Camptoteca acuminata*, a plant originating from China, of the Nyssaceae family. The molecule consists of a pentacyclic structure having a lactone in the E ring, which is essential for cytotoxicity. The drug demonstrated a wide spectrum of antitumor activity, in particular against colon tumors, other solid tumors and leukemias, and the first clinical trials were performed in the early 70's.

Since Camptothecin (CPI) has low water solubility and in order to prepare clinical trials, the National Cancer Institute (NCI) prepared the sodium salt (NSC100880), which is water-soluble. Clinical trials in phase I and II were not completed because of the high toxicity showed by the compound (hemorrhagic cystitis, gastrointestinal toxicity, such as nausea, vomit, diarrhoea, and myelosuppression, especially leucopenia and thrombocytopenia.

Subsequently, many CPT analogues were synthesised in order to obtain compounds with lower toxicity and higher water solubility. Two drugs are marketed, irinotecan (CPT-11) (Camptosar™ by Upjohn) and topotecan (Hycamtin™ or Thycantin™ by Smith Kline & Beecham).

All the derivatives identified to-date contain the parent structure with 5 rings, essential for cytotoxicity. It was demonstrated that modifications on the first ring, such as in the case of the above-mentioned drugs increase water solubility and allow a higher tolerability of the drug.

Patent application WO97/31003 discloses derivatives of camptothecins substituted at positions 7, 9 and 10. Position 7 provides the following substitutions: —CN, —CH(CN)—$R_4$, —CH=C(CN)—$R_4$, —$CH_2$—CH=C(CN)—$R_4$, —C(=NOH)—$NH_2$, —CH=C($NO_2$)—$R_4$, —CH($CH_2NO_2$)—$R_4$, 5-tetrazolyl, 2-(4,5-dihydroxazolyl), 1,2,4-oxadiazolidin-3-yl-5-one, wherein $R_4$ is hydrogen, linear or branched alkyl from 1 to 6 carbon atoms, nitrile, carboxyalkoxy.

Of these compounds, the best one proved to be the 7-nitrile (7-CN), hereinafter named CPT 83, with cytotoxic activity on non-small cells lung carcinoma (non-SCLC, H-460). This tumour line is intrinsically resistant to cytotoxic therapy and is only moderately responsive topoisomerase I inhibitors, notwithstanding the overexpression of the target enzyme. CPT 83 is more active than topotecan, taken as reference compound and on the whole it offers a better pharmacological profile, even in terms of tolerability, then a better therapeutic index.

CPT 83 is prepared trough a synthesis route comprising the oxidation of 7-hydroxymethylcamptothecin to camptothecin 7-aldehyde, the transformation of the latter into oxime and final conversion into nitrile.

The starting compound and the intermediates are disclosed in Sawada et al., *Chem. Pharm. Bull.*, 39, 5272 (1991). This paper makes reference to a patent family with priority of 1981, for example European patent application EP 0056692, published in 1982. In these publications camptothecin 7-aldehyde and its oxime are described among others.

The usefulness of these derivatives is to provide compounds with anti-tumor activity having low toxicity starting from 7-hydroxymethylcamptothecin. In the paper published on Chem. Pharm. Bull. 39, 5272 (1991), the authors demonstrate that, with respect to camptothecin, the 7-alkyl and 7-acyloxymethyl derivatives, which were not foreseen in the above mentioned patent application, are the more active compounds on lines of murine leukemia L1210, while lower activity, always with respect to camptothecin, was observed in compounds bearing 7-substitutions with high polar character, such as hydrazones and the oxime —CH(=NOH).

In patent application EP1044977 and in Dallavalle S. et al., *J. Med. Chem.* 2001, 44, 3264-3274, camptothecin derivatives are described which bear an alkyloxime O-substituted at position 7 and which are endowed with antitumor activity higher than the compound of reference topotecan. Moreover these camptothecin derivatives bearing an imino group on position 7, also show an improved therapeutic index. Among these compounds one of the preferred molecules was shown to be 7-t-butoxyiminomethylcamptothecin (CPT 184). When this molecule is prepared as described in EP1044977 and in the above Dallavalle paper, a mixture of the two E and Z isomers, in 8:2 ratio, is obtained from a solvent mixture containing ethanol and pyridine.

All the processes described in the above-mentioned literature for obtaining camptothecin derivatives bearing alkyloxime O-substituted at position 7 lead to a mixture of the two E and Z isomers of the oxime or the alkyloxime.

Therefore, it is desirable to make available a stereoselective process leading to single E,Z isomers, respectively, more particularly the E isomer.

Many drugs, old and new, were discovered and rushed into market as their 'suitable' crystalline forms and had never been screened thoroughly for their potential polymorphic forms. With the recent technological advancement of solid state chemistry, it is possible that new polymorphic forms can be discovered, which have never been seen before. The new polymorphic forms are often able to deliver therapeutic advantages and represent one of the new challenges of the pharmaceutical industry. As a matter of fact polymorphism, the ability of a molecule to crystallize into more than one crystal arrangement, can have a profound effect on the shelf life, solubility, formulation properties, and processing properties of a drug. More seriously, the action of a drug can be affected by the polymorphism of the drug molecules. Different polymorphs can have different rates of uptake in the body, leading to lower or higher biological activity than desired. In extreme cases, an undesired polymorph can even be toxic. The occurrence of an unknown polymorphic form during manufacture can have an enormous impact on a drug company. Therefore it is vital that researchers involved in the formulation of crystalline products be able to select the polymorph with the correct properties and anticipate problems such as the unwanted crystallization of other polymorphs. Surprisingly, a very large number of pharmaceuticals exhibit the phenomenon of polymorphism. 70% of barbiturates, 60% of sulfonamides and 23% of steroids exist in different polymorphic forms.

The problem of polymorphism in organic compounds is generically reviewed by Caira, M. R. "Crystalline Polymorphism of Organic Compounds", Topics in Current Chemistry, Springler, Berlin, Del., Vol. 198, 1998, pages 163-208.

Conducting a crystallization study on gimatecan has brought the Applicant to the claimed invention.

DETAILED DESCRIPTION OF THE INVENTION

Figure 1:
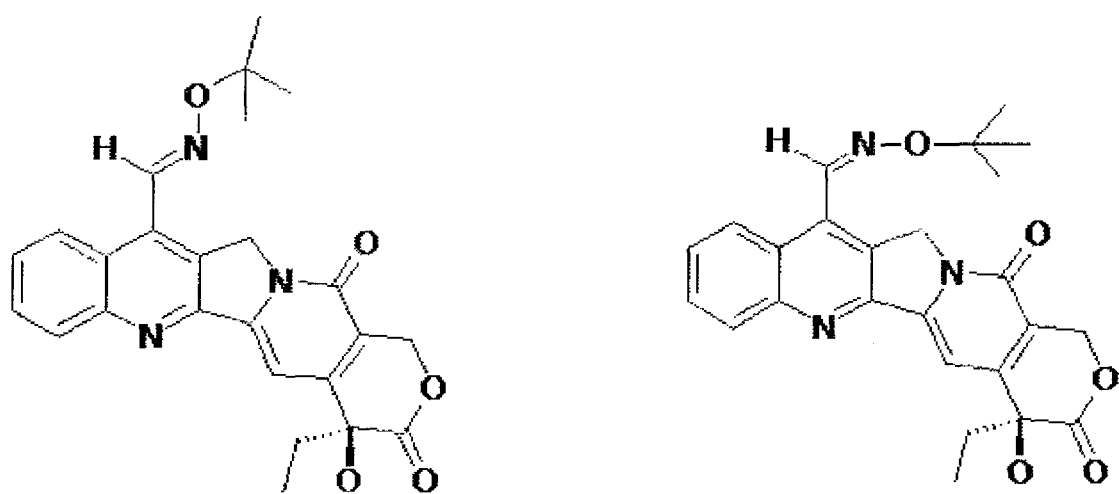
FIG. 1 reports on the left the structural formula of 7-[(E)-t-butyloxyiminomethyl]-camptothecin (gimatecan) and on the right the formula of 7-[(Z)-t-butyloxyiminomethyl]-camptothecin.

We have now surprisingly found a stereoselective process for preparing 7-[(E)-t-butyloxyiminomethyl]-camptothecin (also known as gimatecan). We have also found that it is possible to obtain the complete conversion of the Z isomer into the E isomer. For clarity, the structural formulae of the two isomers are shown in FIG. 1.

Moreover, we found that this product can exist under different crystalline forms and that these forms can be obtained by using the same stereoselective process with the addition of further dissolution and precipitation steps carried out in appropriate different solvent mixtures.

Therefore the main object of the present invention is a process for the stereoselective preparation of 7-[(E)-t-butyloxyiminomethyl]-camptothecin comprising reacting an acetal of 7-formyl-camptothecin with O-t-butylhydroxylamine hydrochloride in a polar protic or aprotic organic solvent, preferably under acidic conditions (pH<7). In fact it has been found that the amount of Z isomer is proportional to the amount of base (for example pyridine) added. Therefore the process of the present invention must be carried out in the absence of an organic base, in particular, in the absence of pyridine.

Different embodiments and variations of the above process are comprised in the present invention.

Preferably, the polar protic or aprotic organic solvent is an alcohol, such as methanol, ethanol, n-propanol, i-propanol, n-butanol, i-butanol. More preferably, it is ethanol or methanol.

The pH is preferably acidic, but it can be brought to higher values (close but not equal to 7) with the addition of an inorganic base. Preferably, the inorganic base is sodium or potassium hydroxide. Preferably, the inorganic base is added in a molar ratio of 0.5-0.9:1 with respect to the hydroxylamine hydrochloride.

The acetal of 7-formyl-camptothecin is a dialkyl acetal, preferably methyl or ethyl acetal.

The temperature of the reaction is usually comprised between room temperature and solvent boiling point.

At the end of the reaction the precipitate is isolated from the reaction mixture, for example by filtration.

According to the process of the present invention, the E isomer is always obtained in a ratio of at least 95:5 with respect to the Z isomer. The Examples show that the process of the invention allows to obtain the E isomer up to a ratio of 99.8:0.2 with respect to the Z isomer.

According to a preferred embodiment of the invention the above-described process comprises further steps, such as dissolving the precipitate previously obtained in dichloromethane, adding a co-solvent, concentrating the solution obtained and crystallizing the product thus obtained.

Depending on the co-solvent used, different crystalline forms are obtained as follows.

These different crystalline forms are a further object of the present invention.

| SOLVENTS | Polymorph (by IR and DSC) | Polymorph (by powder X-ray diffraction) |
|---|---|---|
| Acetone | I | I |
| MeOH | III | III |
| EtOH | III | III |
| Hexane | II 75% | II (with a substantial amount of amorphous) |
| EtOAc | II | II |
| Toluene | II | II |
| n-Butyl chloride | II | II |
| Methyl t-butyl ether | II 90% III 10% | II |

Figure 2:
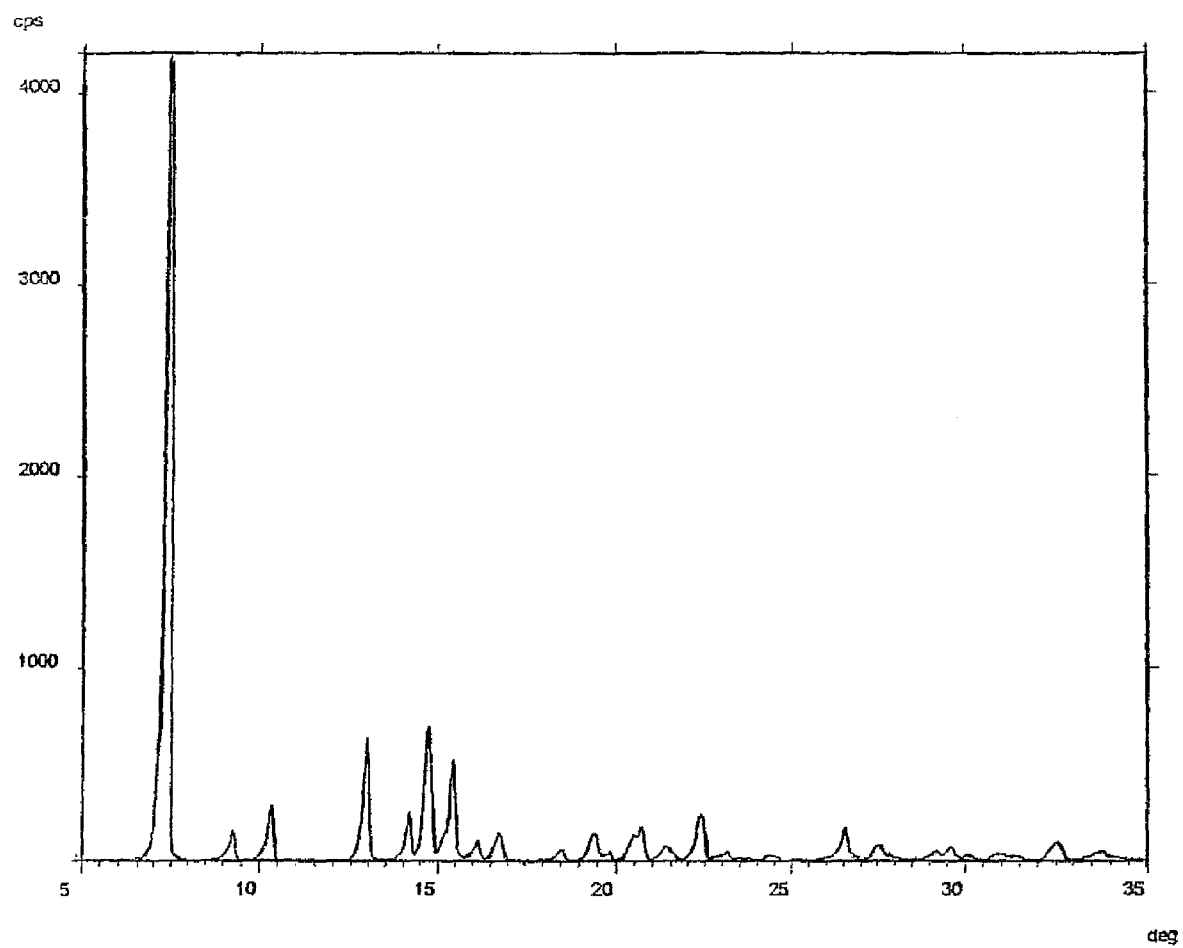
FIG. 2 reports X-ray diffraction pattern of the crystalline form I of 7-[(E)-t-butyloxyiminomethyl]-camptothecin (gimatecan).

Using acetone as co-solvent, crystalline form I of gimatecan is obtained, which is characterized by a powder X-ray diffraction pattern obtained by irradiation with CuK-α1 X-rays, as shown in FIG. 2.

The characteristic main diffraction peaks of this form are given in the following table:

| Degrees 2-Theta | Relative intensity (%) |
|---|---|
| 7.2 | 100 |
| 9.2 | 4.8 |
| 10.2 | 7.3 |
| 12.7 | 16.3 |
| 14.0 | 8.1 |
| 14.7 | 9.5 |
| 15.2 | 13.0 |
| 16.0 | 2.4 |
| 16.7 | 4.06 |
| 19.7 | 3.2 |
| 20.5 | 3.2 |
| 20.7 | 4.06 |
| 22.2 | 6.5 |
| 26.5 | 3.2 |
| 32.5 | 2.4 |

Figure 4:
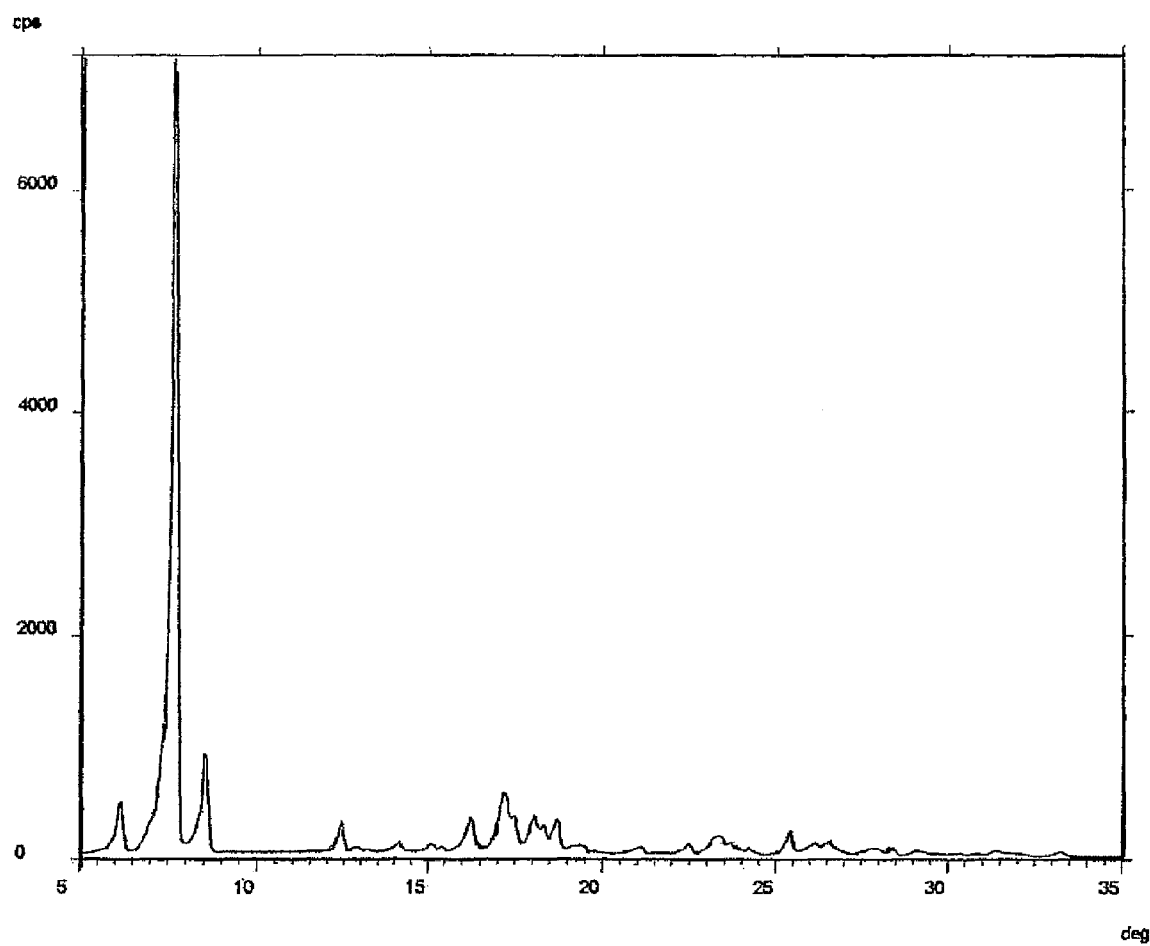
FIG. 4 reports X-ray diffraction pattern of the crystalline form III of 7-[(E)-t-butyloxyiminomethyl]-camptothecin (gimatecan).

Using ethanol or methanol as co-solvent, crystalline form III of gimatecan is obtained, which is characterized by a powder X-ray diffraction pattern obtained by irradiation with CuK-α1 X-rays, as shown in FIG. 4. The characteristic main diffraction peaks of this form are given in the following table:

| Degrees 2-Theta | Relative intensity (%) |
|---|---|
| 6.0 | 1.0 |
| 7.5 | 100.0 |
| 8.51 | 8.1 |
| 12.3 | 4.8 |
| 16.0 | 6.0 |
| 17.0 | 11.0 |
| 18.0 | 6.6 |
| 18.2 | 4.0 |
| 18.7 | 6.0 |

-continued

| Degrees 2-Theta | Relative intensity (%) |
|---|---|
| 23.2 | 2.4 |
| 25.2 | 3.6 |

Figure 3:
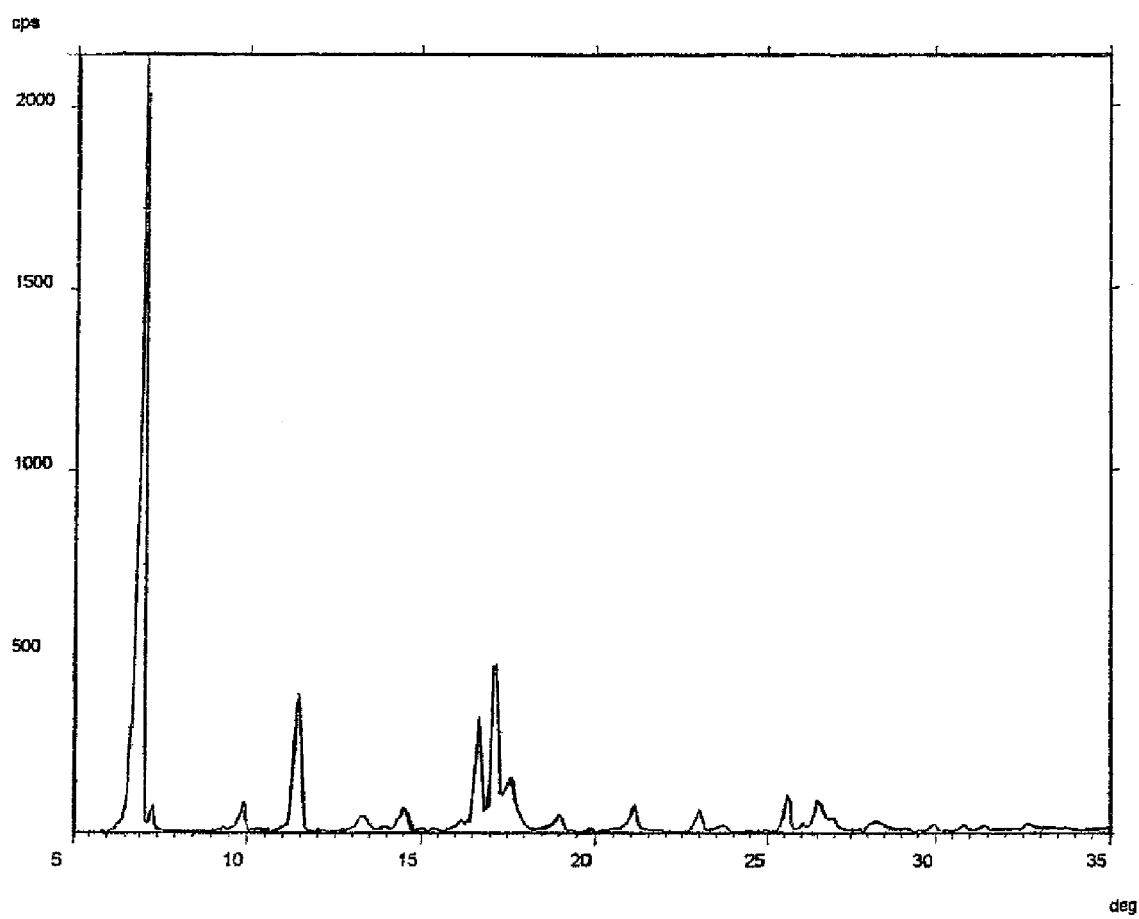
FIG. 3 reports X-ray diffraction pattern of the crystalline form II of 7-[(E)-t-butyloxyiminomethyl]-camptothecin (gimatecan).

Using ethyl acetate, toluene, n-butyl chloride, methyl t-butyl ether or hexane as co-solvent, crystalline form II of gimatecan is obtained, which is characterized by a powder X-ray diffraction pattern obtained by irradiation with CuK-α1 X-rays, as shown in FIG. 3. The characteristic main diffraction peaks of this form are given in the following table:

| Degrees 2-Theta | Relative intensity (%) |
|---|---|
| 6.7 | 100.0 |
| 7.2 | 4.8 |
| 9.7 | 6.0 |
| 11.2 | 24.0 |
| 13.2 | 3.0 |
| 14.5 | 4.8 |
| 16.0 | 2.4 |
| 16.7 | 21.6 |
| 17.0 | 31.2 |
| 17.5 | 10.8 |
| 19.0 | 3.0 |
| 21.0 | 4.8 |
| 23.0 | 3.6 |
| 25.5 | 7.2 |
| 26.5 | 6.0 |
| 28.2 | 3.0 |

These new crystalline forms I, II and III of gimatecan are further objects of the present invention. Crystalline form I of gimatecan is preferred.

Amorphous form I of gimatecan is a further object of the present invention.

Another object of the present invention is the use of any crystalline form I, II, III of gimatecan, or a mixture thereof, as medicaments, in particular for the preparation of a medicament for treating pathological states which arise from or are exacerbated by cell proliferation.

A further object of the present invention are compositions, in particular pharmaceutical compositions, comprising at least one of the above-mentioned crystalline forms as active ingredient, the pharmaceutical compositions being in admixture with at least one pharmaceutically acceptable carrier and/or diluent. In addition, pharmaceutical compositions of the present invention can contain also one or more pharmaceutically acceptable excipients.

Gimatecan shows an antiproliferative activity, therefore its crystalline forms are useful for their therapeutical activity, and possess physicochemical properties that make them suitable to be formulated in pharmaceutical compositions.

The pharmaceutical compositions comprise at least one of the above-mentioned crystalline forms of gimatecan, in an amount such as to produce a significant therapeutical effect, in particular antitumoral effect. The compositions comprised within the present invention are conventional and are obtained with commonly used methods in the pharmaceutical industry. According to the desired administration route, the compositions shall be in solid or liquid form, suitable to the oral, parenteral, intravenous route. The compositions according to the present invention comprise together with the active ingredients at least a pharmaceutically acceptable vehicle or excipient. Formulation coadjuvants, for example solubilizing, dispersing, suspending, emulsionation agents can be particularly useful.

The above-mentioned crystalline forms of gimatecan can also be used in combination with other active ingredients, for example other anti-tumor drugs, both in separate forms, and in a single dose form.

The above-mentioned crystalline forms of gimatecan according to the present invention are useful as medicaments with antitumor activity, for example in lung tumors, such as the non-small cell lung tumour, tumors of the colon-rectum, prostate, gliomas.

Cytotoxic activity is assayed in cell systems of human tumour cells, using the antiproliferative activity test as a method of evaluation of the cytotoxic potential.

These and other objects of the present invention shall be illustrated in detail also by means of the following Examples.

The following examples further illustrate the invention.

INTRODUCTION

Example 1 and 2 deal with the synthesis of 7-[(E)-t-butyloxyiminomethyl]-camptothecin employing 7-formyl-camptothecin dimethylacetal as starting material.

Examples 3 and 4 report the synthesis of 7-[(E)-t-butyloxyiminomethyl]-camptothecin employing 7-formyl-camptothecin as starting material under conditions that afforded the E isomer. All the reactions of this group are faster then the reactions reported in Examples 1 and 2, indicating that hydrolysis of the acetal is plausibly slower than the reaction of the aldehyde to give the oxime.

Example 5 reports the conversion of the Z isomer into the E isomer.

Example 6 reports the synthesis and the characterization of the different (polymorphic) crystalline forms that can be obtained for 7-[(E)-t-butyloxyiminomethyl]-camptothecin (gimatecan).

HPLC: the analyses are carried out on an instrument equipped with a quaternary pump (Waters Alliance 2690) with automatic injector (injected volume 5 µl) and with a UV detector operating at 260 nm (Waters 2487) controlled by the software Waters 'Empower Pro'.

A C18 reverse phase column (Symmetry C18; 75×4.6 mm Waters) is used with a linear elution gradient (see table below), with 1.0 ml/min flow rate.

Gradient Program

A: $H_2O/CH_3CN$ 60140 (v/v)
B: $H_2O/CH_3CN$ 30170 (v/v)

| Time (min) | % A | % B |
|---|---|---|
| 0 | 100 | 0 |
| 30 | 100 | 0 |
| 40 | 0 | 100 |
| 45 | 100 | 0 |
| 50 | 100 | 0 |

The retention time of 7-[(E)-tert-butyloxyiminomethyl]-camptothecin is 12 minutes, and the retention time of the Z-isomer is 8 minutes.

Example 1

Preparation of 7-[(E)-tert-butyloxyiminomethyl]-camptothecin from 7-formylcamptothecin-dimethylacetal 7-Formyl-camptothecin-dimethylacetal (500 mg; 1.2 mmol) and O-tertbutylhydroxylamine hydrochloride (372 mg; 2.9 mmol) were added to 95% ethanol (12.5 ml) in a three-necked flask, protected from light and equipped with a magnetic stirrer and a condenser. The mixture was heated to reflux for 4 h. HPLC analysis showed a E:Z ratio 99.8:0.2. The crude product was obtained as precipitated from the reaction mixture and isolated by filtration. After chromatographic purification on silica gel (20 g), eluting with dichloromethane-methanol 95:5, gimatecan (460 mg) was obtained as a yellow powder (yield: 87%).

Example 2

Preparation of 7-[(E)-tert-butyloxyiminomethyl]-camptothecin from 7-formylcamptothecin-dimethylacetal 7-Formyl-camptothecin-dimethylacetal (500 mg; 1.2 mmol), O-tertbutylhydroxylamine hydrochloride (372 mg; 2.9 mmol) and sodium hydroxide (59 mg; 1.47 mmol) were added to 95% ethanol (12.5 ml) in a three-necked flask, protected from light and equipped with a magnetic stirrer and a condenser. The mixture was heated to reflux 24 h. HPLC analysis showed a E:Z ratio 98.8:1.2. The crude product was obtained as precipitated from the reaction mixture and isolated by filtration. After chromatographic purification on silica gel (20 g), eluting with dichloromethane-methanol 95:5, gimatecan was obtained as a yellow powder (yield: 80%)

Example 3

Reference Example

Preparation of 7-[(E)-tert-butyloxyiminomethyl]-camptothecin from 7-formylcamptothecin 7-Formyl-camptothecin (500 mg; 1.33 mmol), O-tert-butylhydroxylamine hydrochloride (417 mg; 3.3 mmol) and sodium hydroxide (67 mg; 1.65 mmol) were added to 95% ethanol (12.5 ml) in a three-necked flask, protected from light and equipped with a magnetic stirrer and a condenser.

The mixture was heated to reflux for 2 hours. HPLC analysis showed a E:Z ratio 97.4:2.6. The crude product was obtained as precipitated from the reaction mixture and isolated by filtration. After chromatographic purification on silica gel (20 g), eluting with dichloromethane-methanol 95:5, gimatecan (480 mg) was obtained as a yellow powder (yield: 80%).

Example 4

Reference Example

Preparation of 7-[(E)-tert-butyloxyiminomethyl]-camptothecin from 7-formylcamptothecin 7-Formyl-camptothecin (500 mg; 1.33 mmol), O-tert-butylhydroxylamine hydrochloride (417 mg; 3.3 mmol) and sodium hydroxide (120 mg; 3 mmol) were added to 95% ethanol (12.5 ml) in a three-necked flask, protected from light and equipped with a magnetic stirrer and a condenser.

The mixture was heated to reflux for 2 hours. HPLC analysis showed a E:Z ratio 95.5. The crude product was obtained as precipitated from the reaction mixture and isolated by filtration. After chromatographic purification on silica gel (20 g), eluting with dichloromethane-methanol 95:5, gimatecan (550 mg) was obtained as a yellow powder (yield: 93%).

Example 5

Isomer Conversion

7-[(Z)-tert-butyloxyiminomethyl]-camptothecin (100 mg) was dissolved in dichloromethane (30 ml). Hydrochloric acid (0.2 ml) was added at room temperature and the mixture was subjected to irradiation with a 125 W Hg high pressure U.V. lamp for 1 hour. The HPLC analysis showed that Z-isomer was completely converted into the E-isomer.

Example 6

Crystallization Studies

7-[(E)-tert-butyloxyiminomethyl]-camptothecin (2.5 g) was dissolved in of dichloromethane (500 ml). A co-solvent (500 ml) was added to the solution, then by means of a rotavapor, the mixture was concentrated at a temperature of 40° C. up to a volume of 250 ml.

The suspension was kept under stirring at room temperature for 30 minutes, then the solid formed was filtered by washing twice with 20 ml of the co-solvent. After one night in an oven at 50° C. under vacuum, 2.1 g of product were obtained.

The co-solvents used were the following: acetone, ethanol, methanol, ethyl acetate, toluene, n-butylchloride, methyl tert-butyl ether, and hexane.

The crystals obtained were analyzed by X-ray powder Diffractometry. The diffractograms were obtained on 20-50 mg of powder by using a Siemens D-500 computer controlled diffractometer equipped with a CuK-α radiation source monochromated with (002) graphite crystals, with Sollers slits and narrow (0.3°) divergence and receiving apertures. The confidence limits of the scattering angles are ±0.5 2-Theta.

Samples obtained using acetone as co-solvent (form I) gave the following results.

The X-ray powder diffractogram is characteristic of a crystalline substance. The characteristic main diffraction peaks of this form are given in the following table:

| Degrees 2-Theta | Relative intensity (%) |
| --- | --- |
| 7.2 | 100 |
| 9.2 | 4.8 |
| 10.2 | 7.3 |
| 12.7 | 16.3 |
| 14.0 | 8.1 |
| 14.7 | 19.5 |
| 15.2 | 13.0 |
| 16.0 | 2.4 |
| 16.7 | 4.06 |
| 19.7 | 3.2 |
| 20.5 | 3.2 |
| 20.7 | 4.06 |
| 22.2 | 6.5 |
| 26.5 | 3.2 |
| 32.5 | 2.4 |

Samples obtained using ethanol or methanol as cosolvent (form III) gave the following results.

The X-ray powder diffractogram is characteristic of a crystalline substance. The characteristic main diffraction peaks of this form are given in the following table:

| Degrees 2-Theta | Relative intensity (%) |
| --- | --- |
| 6.0 | 11.0 |
| 7.5 | 100.0 |
| 8.5 | 18.1 |
| 12.3 | 4.8 |
| 16.0 | 6.0 |
| 17.0 | 11.0 |
| 18.0 | 6.6 |
| 18.2 | 4.0 |
| 18.7 | 6.0 |
| 23.2 | 2.4 |
| 25.2 | 3.6 |

Samples obtained using ethyl acetate, toluene, n-butyl chloride, methyl t-butyl ether or hexane as cosolvent (form II) gave the following results.

The X-ray powder diffractogram is characteristic of a crystalline substance. The characteristic main diffraction peaks of this form are given in the following table:

| Degrees 2-Theta | Relative intensity (%) |
| --- | --- |
| 6.7 | 100.0 |
| 7.2 | 4.8 |
| 9.7 | 6.0 |
| 11.2 | 24.0 |
| 13.2 | 3.0 |
| 14.5 | 4.8 |
| 16.0 | 2.4 |
| 16.7 | 21.6 |
| 17.0 | 31.2 |
| 17.5 | 10.8 |
| 19.0 | 3.0 |
| 21.0 | 4.8 |
| 23.0 | 3.6 |
| 25.5 | 7.2 |
| 26.5 | 6.0 |
| 28.2 | 3.0 |

To further characterize these crystalline forms of gimatecan, the same samples were examined by IR spectroscopy. In the following table are given the peaks ($cm^{-1}$) characteristic of the three forms.

| Form I (acetone) Frequency ($cm^{-1}$) | Form II (AcOEt)* Frequency ($cm^{-1}$) | Form III (EtOH)** Frequency ($cm^{-1}$) |
| --- | --- | --- |
| 1751.7 | 1761.7 | 1739.3 |
| 1606.4 | 1605.0 | 1619.8 |
| 1162.2 | 1156.7 | 1154.4 |
| 766.2 | 764.3 | 759.5 |

*identical data are observed also for the forms obtained from toluene, n-butyl chloride, methyl t-butyl ether or hexane
**identical data are observed also for the form obtained from methanol IR spectra were collected at 4 $cm^{-1}$ on 1% KBr pellet with a Perkin Elmer Spectrum 1000 FT-IR

The invention claimed is:

1. A compound which is crystalline form I of 7-[(E)-t-butyloxyiminomethyl]-camptothecin wherein said compound shows on X-ray diffraction a peak at an angle of refraction 2 theta (θ), of 7.2±0.2 degrees.

2. The compound according to claim 1, having an X-ray diffraction pattern, expressed in terms of 2 θ angles, that includes five or more peaks selected from the group consisting of about 10.2, 12.7, 14.0, 14.7 and 15.2±0.02 degrees.

3. The compound according to claim 1 having substantially the same X-ray diffraction pattern as shown in FIG. 2.

4. A composition comprising a compound of claim 1.

5. A pharmaceutical composition comprising:
   (a) a compound of claim 1; and
   (b) a pharmaceutically acceptable carrier or diluent.

6. The pharmaceutical composition according to claim 5, further comprising one or more pharmaceutically acceptable excipients.

7. The pharmaceutical composition according to claim 5, which is a dosage form suitable for oral administration.

8. The pharmaceutical composition according to claim 7, wherein said dosage form is selected from a tablet, capsule or solution.

9. A process for the stereo selective preparation of the compound according to claim 1 comprising reacting an acetal of 7-formyl-camptothecin with O-t-butylhydroxylamine hydrochloride in a polar protic or aprotic organic solvent.

10. The process according to claim 9, wherein said reaction is carried out in acidic conditions.

11. The process according to claim 9, wherein the polar protic organic solvent is an alcohol.

12. The process according to claim 9, wherein the polar protic organic solvent is ethanol or methanol.

13. The process according to claim 9, wherein an inorganic base is added to the reaction medium in a molar ratio of 0.5-0.9:1 with respect to the hydroxylamine hydrochloride.

14. The process according to claim 13, wherein the inorganic base is sodium or potassium hydroxide.

15. The process according to claim 13, wherein a precipitate is isolated from the reaction mixture by filtration.

16. The process according to claim 9, wherein the acetal of 7-formyl-camptothecin is a dialkyl acetal.

17. The process according to claim 9, wherein the acetal of 7-formyl-camptothecin is dimethyl or diethyl acetal.

18. The process according to claim 9, wherein the reaction temperature is kept between room temperature and solvent boiling point.

19. The process according to claim 9, wherein at the end of the reaction a precipitate is isolated from the reaction mixture.

20. The process according to claim 19, wherein the precipitate is isolated from the reaction mixture by filtration.

21. The process according to claim 19, further comprising dissolving the precipitate in dichloromethane, adding a co-solvent, concentrating the solution so obtained and allowing the reaction product to precipitate and crystallize.

22. The process according to claim 21, in which the co-solvent is acetone.

* * * * *

UNITED STATES PATENT AND TRADEMARK OFFICE
CERTIFICATE OF CORRECTION

PATENT NO.       : 7,799,921 B2                                       Page 1 of 1
APPLICATION NO.  : 11/721282
DATED            : September 21, 2010
INVENTOR(S)      : Carminati et al.

It is certified that error appears in the above-identified patent and that said Letters Patent is hereby corrected as shown below:

Column 10, line 23, claim 2,
"five" should read --one--

Signed and Sealed this
Eleventh Day of October, 2011

David J. Kappos
*Director of the United States Patent and Trademark Office*